US010004397B2

United States Patent
Gramatikov et al.

(10) Patent No.: US 10,004,397 B2
(45) Date of Patent: Jun. 26, 2018

(54) METHOD AND SYSTEM FOR IMPROVING AIMING DURING OPTICAL COHERENCE TOMOGRAPHY ON YOUNG CHILDREN BY SYNCHRONIZATION WITH RETINAL BIFRINGENCE SCANNING

(71) Applicants: THE JOHNS HOPKINS UNIVERSITY, Baltimore, MD (US); DUKE UNIVERSITY, Durham, NC (US)

(72) Inventors: Boris Gramatikov, Baltimore, MD (US); David Lee Guyton, Baltimore, MD (US); Kristina Irsch, Baltimore, MD (US); Cynthia Toth, Chapel Hill, NC (US); Oscar Carrasco-Zevallos, Durham, NC (US); Joseph Izatt, Raleigh, NC (US)

(73) Assignees: The Johns Hopkins University, Baltimore, MD (US); Duke University, Durham, NC (US)

( * ) Notice: Subject to any disclaimer, the term of this patent is extended or adjusted under 35 U.S.C. 154(b) by 0 days. days.

(21) Appl. No.: 15/026,688

(22) PCT Filed: Oct. 2, 2014

(86) PCT No.: PCT/US2014/058756
§ 371 (c)(1),
(2) Date: Apr. 1, 2016

(87) PCT Pub. No.: WO2015/051077
PCT Pub. Date: Apr. 9, 2015

(65) Prior Publication Data
US 2016/0235292 A1    Aug. 18, 2016

Related U.S. Application Data

(60) Provisional application No. 61/885,794, filed on Oct. 2, 2013.

(51) Int. Cl.
*A61B 3/14* (2006.01)
*A61B 3/10* (2006.01)
(Continued)

(52) U.S. Cl.
CPC ............ *A61B 3/102* (2013.01); *A61B 3/0025* (2013.01); *A61B 3/0041* (2013.01);
(Continued)

(58) Field of Classification Search
CPC ..... A61B 3/102; A61B 3/0025; A61B 5/7285; A61B 3/0091; A61B 3/113; A61B 3/152; A61B 3/0041; A61B 3/1225
(Continued)

(56) References Cited

U.S. PATENT DOCUMENTS 6,027,216 A     2/2000   Guyton et al.
2010/0110377 A1  5/2010   Maloca et al.
(Continued)

*Primary Examiner* — Tuyen Tra
(74) *Attorney, Agent, or Firm* — Johns Hopkins Technology Ventures

(57) ABSTRACT

The present invention is directed to a method and system for improved aiming during Optical Coherence Tomography (OCT) on young children and those unable to cooperate with OCT imaging by synchronization with retinal birefringence scanning (RBS). OCT is performed without knowing whether or not the subject is looking at the intended target. The present invention combines OCT retinal imaging, such as, but not limited to, time domain OCT, SDOCT, or SSOCT, with RBS technology that provides accurate information on the presence or absence of foveal fixation. Therefore, the present invention only analyzes data during foveal fixation. A system combining OCT with RBS is implemented such that both systems co-operate in a specified alignment, such that when the RBS fixation detection system detects alignment with the fovea of the eye, the OCT system will be aimed at the retinal region of interest, usually but not necessarily including the macular area.

20 Claims, 2 Drawing Sheets

(51) Int. Cl.
*A61B 3/12* (2006.01)
*A61B 3/00* (2006.01)
*A61B 3/113* (2006.01)
*A61B 3/15* (2006.01)
*A61B 5/00* (2006.01)

(52) U.S. Cl.
CPC ............ *A61B 3/0091* (2013.01); *A61B 3/113* (2013.01); *A61B 3/1225* (2013.01); *A61B 3/152* (2013.01); *A61B 5/7285* (2013.01)

(58) Field of Classification Search
USPC ............ 351/208, 206, 205, 200, 45; 396/18
See application file for complete search history.

(56) References Cited

U.S. PATENT DOCUMENTS

| | | |
|---|---|---|
| 2011/0105868 A1 | 5/2011 | Westphal |
| 2012/0229768 A1 | 9/2012 | Gramatikov et al. |
| 2013/0107209 A1 | 5/2013 | Hacker et al. |
| 2017/0105617 A1* | 4/2017 | Li ........................ A61B 3/0025 |

* cited by examiner

METHOD AND SYSTEM FOR IMPROVING AIMING DURING OPTICAL COHERENCE TOMOGRAPHY ON YOUNG CHILDREN BY SYNCHRONIZATION WITH RETINAL BIFRINGENCE SCANNING

CROSS-REFERENCE TO RELATED APPLICATIONS

This application is a 35 U.S.C. § 371 U.S. national entry of International Application PCT/US2014/058756, having an international filing date of Oct. 2, 2014, which claims the benefit of U.S. Provisional Application No. 61/885,794, filed Oct. 2, 2013, the content of each of the aforementioned applications is herein incorporated by reference in their entirety.

FIELD OF THE INVENTION

The present invention relates generally to medical imaging. More particularly, the present invention relates to a method and system for imaging the macular region of the eye.

BACKGROUND OF THE INVENTION

Today, if a retinal condition is suspected in an infant or toddler, the challenge to the ophthalmologist is to enable the child to achieve and maintain ocular fixation long enough for proper examination. To obtain a precise retinal examination, the choices are placing a child under general anesthesia (with many risks, such as pneumonia and potential death), perform a limited examination, or worse, to wait until the child grows older to identify what is wrong. For adults, where fixation and cooperation are usually not an issue, a technology known as optical coherence tomography (OCT) is used to provide 3-dimensional, and magnified cross-sectional images of the retina (e.g., images depicting the macula—FIG. 1). This standard of care for outpatient diagnosis and management of retinal disease in adults is generally well-tolerated in older children.

Most neonates can be adequately immobilized for retinal imaging, although not perfectly so. Infants, active toddlers and young children will not cooperate for such imaging, and thus a more suitable version of the OCT instrument is needed. Indeed, there may also be patients in other age groups unable to sit and hold still for such imaging. It is distressing that treatable retinal conditions in young children and those who cannot cooperate with traditional OCT exams are frequently missed because of this situation.

Due to the large amount of data needed to be processed after acquisition, conventional OCT (including spectral domain OCT and even Swept Source OCT) does not allow monitoring of the 2D/3D images in real time. This means that in the context of young children and those unable to cooperate for OCT imaging, several seconds of 3D data need to be first collected blindly, without information as to whether the OCT system's image includes the fovea (the most sensitive and critical retinal region, in the center of the macula), i.e. without knowing whether or not the child is actually looking at the intended target.

Accordingly, there is a need in the art for a system and method configured to obtain OCT images, specifically, during confirmed foveal fixation.

SUMMARY OF THE INVENTION

The foregoing needs are met by the present invention which provides a system combining Optical Coherence Tomography (OCT, SDOCT, SSOCT) with a Retinal Birefringence Scanning fixation detection system. In accordance with the system of the present invention, the OCT and RBS systems cooperate in a specified alignment, such that when the RBS fixation detection system detects alignment with the fovea of the eye, the OCT system will be aimed at the retinal region of interest, usually but not necessarily including the macular area. For example, the region of interest might be centered upon the optic disc instead of upon the macula, with the optic disc located approximately 15 degrees nasal to the center of the macula.

In accordance with an aspect of the present invention, in the combination of a retinal-birefringence-scanning fixation detection optical system with a scanning optical coherence tomography optical system, the exit pupils of said two systems, within which exit pupils the respective scanning beams pivot, are substantially coincident with one another, and wherein said coincident exit pupils are further arranged to be moved together to be coincident with the pupil of the eye being examined In accordance with another aspect of the present invention, a method of synchronization between the two systems is configured such that detection of foveal fixation by the RBS system is signaled to the OCT system, thus enabling OCT data collection only during foveal fixation.

In accordance with another aspect of the present invention, a method of communication between the two systems, where OCT data are being collected continuously, while also an additional synchro-channel from the RBS system is recorded, carrying information about the presence or absence of foveal fixation. Then, during RBS-guided OCT analysis and reconstruction, only time intervals of foveal fixation are processed, thus reducing analysis time.

In accordance with yet another aspect of the present invention a method includes presenting fixation targets to the test subject during OCT data collection by means of a continuous movie aligned with the center of the RBS fixation detection scan.

In accordance with an aspect of the present invention, a system for imaging a fovea of a retina of a subject includes a system configured for optical coherence tomography (OCT), such that OCT data related to the fovea of the retina of the subject are collected. The system for imaging a fovea also includes a system configured for retinal birefringence scanning. Both the system configured for OCT and the system configured for RBS are further configured to cooperate in a specified alignment such that when the RBS fixation detection system detects alignment with the fovea of the eye, the OCT system will be aimed at a retinal region of interest, such that image collection is only executed during a period of foveal fixation of the subject.

In accordance with another aspect of the present invention, the system for imaging a fovea further includes an exit pupil of the system configured for OCT and an exit pupil of the system configured for RBS being substantially coincident with one another. The exit pupil of the system configured for OCT and an exit pupil of the system configured for RBS are also configured to be moved together to be coincident with a pupil of an eye being examined. An image display device is included to attract and maintain the interest of the subject, such that the fovea is attracted into the desired alignment with the RBS fixation detection system, whereby a retinal region of interest is imaged. Additionally, the system configured for RBS signals a presence of foveal fixation to the system configured for OCT, thus triggering data collection.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a method and system for improved aiming during Optical Coherence Tomography (OCT) on the eyes of young children and other patients who cannot cooperate with traditional OCT exams, by synchronization with retinal birefringence scanning (RBS). Contemporary OCT is performed without information as to whether the OCT system is centered on the fovea (the most sensitive, critical retinal region, in the center of the macula), that is without knowledge of whether or not the subject is looking at the intended target. The present invention combines OCT retinal imaging, such as, but not limited to, time domain OCT, SDOCT, or SSOCT, with RBS technology that provides accurate information on the presence or absence of foveal fixation. Therefore, the present invention may be configured to collect OCT data only during foveal fixation. Alternatively, simultaneously recorded information on the presence or absence of foveal fixation can help identify segments of continuously recorded OCT data when foveal fixation is present. A system combining OCT with RBS is implemented such that both systems cooperate in a specified alignment such that when the RBS fixation detection system detects alignment with the fovea of the eye, the OCT system will be aimed at the retinal region of interest. Because the OCT image covers at least 15-20 degrees, it may be advantageous for the image of the macula to be near one edge of the OCT image rather than always in the very center of the OCT image.

Figure 1:
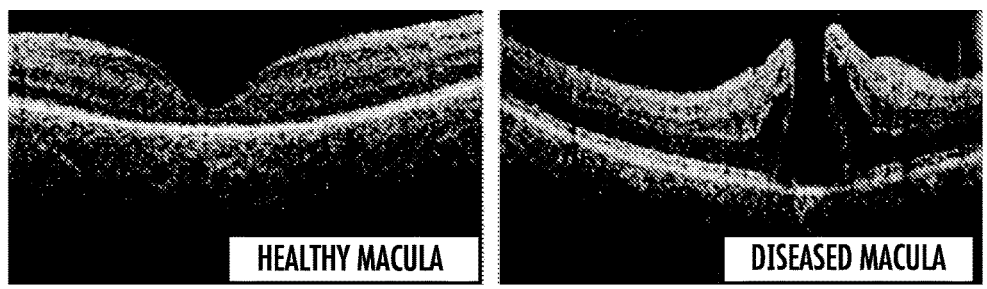
FIG. 1 illustrates images of a healthy macula and a diseased macula.
Figure 2:
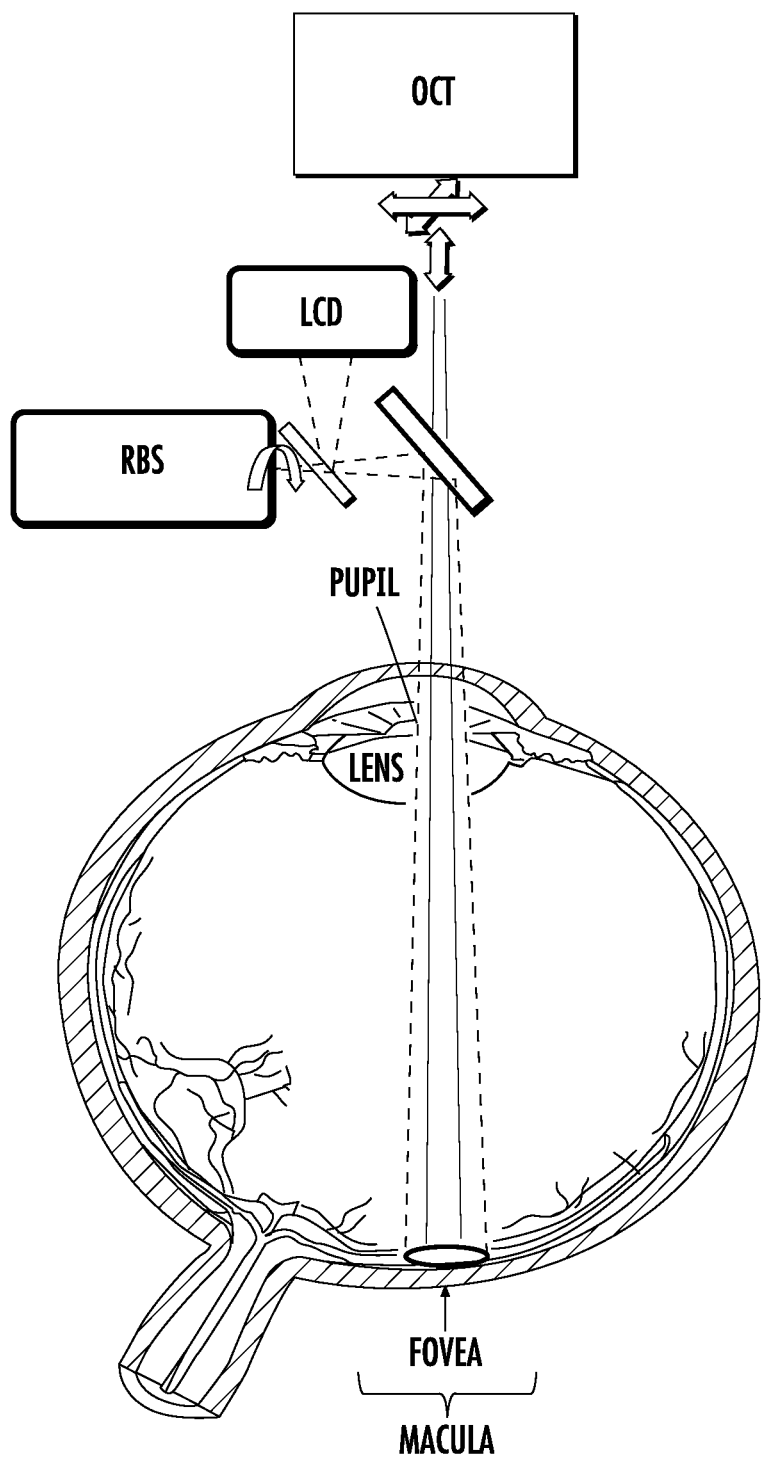
FIG. 2 illustrates a schematic diagram of OCT combined with RBS for imaging a fovea during foveal fixation, according to an embodiment of the present invention.

As noted above, a system and method according to the present invention combines OCT (time domain OCT, SDOCT, or SSOCT) retinal imaging with RBS technology that provides accurate information on the presence or absence of foveal fixation (FIG. 2). In RBS, typically a spot of near-infrared polarized light is scanned in a circle on the retina. The polarization signature of the retroreflected light depends on the precise area of the retina being illuminated (scanned). Foveal fixation (when the patient's eye is looking at the center of the scanned circle of light) is indicated by the presence of characteristic frequency components in the polarization signature of the signal returned, that are multiples or multiples of a fraction of the scanning frequency. The RBS subsystem signals the presence of foveal fixation to the OCT subsystem, thus triggering data collection. Throughout the examination, the unsuspecting child is typically viewing a cartoon on a small LCD computer screen, with specific attention/fixation-locking targets appearing periodically in the center of the screen while the main movie fades away. The examiner is thus able to obtain optical alignment of the OCT device with the child's eye.

The OCT system scans a beam of infrared light across the retina in a raster pattern to capture its image, with the optics of the OCT system arranged such that this beam of light pivots about a small optically-defined, aerial "exit pupil" external to the instrument that is mechanically moved to fit within the pupil of the eye being examined. The RBS fixation detection system scans a different beam of light onto the retina, usually near-infrared, usually in a circular scan pattern on the retina, also through an optically-defined, aerial "exit pupil" that is substantially centered on the pupil of the eye. The RBS fixation detection system also includes a visible-light fixation target, arranged to appear exactly in the center of the faint ring of near-infrared light that the patient sees, such that when the patient looks directly at the visible fixation target, the circular scan of near infrared light becomes centered upon the fovea of the patient's eye, and foveal fixation is detected by the RBS system.

The novel combination of the RBS fixation detection system and the OCT system is thus accomplished by optically arranging for the exit pupils of the two systems to coincide with each other and with the pupil of the eye being examined, and further arranged for the direction of fixation that is detected by the RBS fixation detection system to be aligned with the desired position of the fovea image within the OCT scanned image, not necessarily in the center of the OCT image.

This clinically suitable imaging method allows not only diagnosis of retinal diseases in young patients and in other patients who cannot cooperate with traditional OCT exams, but also monitoring of the progression or response to ocular therapy without a need for sedation or anesthesia.

The many features and advantages of the invention are apparent from the detailed specification, and thus, it is intended by the appended claims to cover all such features and advantages of the invention which fall within the true spirit and scope of the invention.

Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for imaging a region of interest of a retina of a subject comprising:
   a system configured for optical coherence tomography (OCT), such that OCT data related to the retina of the subject is collected;
   a system configured for retinal-birefringence-scanning (RBS) fixation detection; and, wherein, both the system configured for OCT and the system configured for RBS fixation detection are further configured to cooperate in a specified alignment, such that when the RBS fixation detection system detects alignment with a fovea of the eye, the OCT system will be aimed at the retinal region of interest, including a macular area.

2. The system for imaging the region of interest of the retina of the subject of claim 1 wherein the system for OCT and RBS fixation detection are configured such that OCT image collection is only executed during a period of foveal fixation of the subject.

3. The system for imaging the region of interest of the retina of the subject of claim 1 wherein the system for OCT and system for RBS fixation detection are configured such that data is continuously and synchronously recorded from the OCT system and from the RBS fixation detection system, whereby periods of foveal fixation detected by the RBS fixation detection system can be used to identify synchronized portions of the OCT data that will yield images of the region of interest of the retina.

4. The system for imaging the region of interest of the retina of the subject of claim 1 further comprising an exit pupil of the system configured for OCT and an exit pupil of the system configured for RBS being substantially coincident with one another.

5. The system for imaging the region of interest of the retina of the subject of claim 4 further comprising the exit pupil of the system configured for OCT and an exit pupil of the system configured for RBS being configured to be moved together to be coincident with a pupil of an eye being examined.

6. The system for imaging the region of interest of the retina of the subject of claim 1 further comprising an image display device to attract and maintain interest of the subject toward a center of the RBS fixation detection system, such that the retinal region of interest, in known spatial relationship to the fovea, is imaged.

7. The system for imaging the region of interest of the retina of the subject of claim 1 wherein the system configured for RBS signals a presence of foveal fixation to the system configured for OCT, thus triggering data collection.

8. A system for imaging a region of interest of a retina of a subject comprising:
 a system configured for optical coherence tomography (OCT), such that OCT data related to the retina of the subject is collected;
 a system configured for retinal-birefringence-scanning (RBS) fixation detection; and,
 wherein, the system configured for OCT and the system configured for RBS comprise exit pupils and within these exit pupils respective scanning beams pivot, the exit pupils are substantially coincident with one another, and wherein the exit pupils are further arranged to be moved together to be coincident with a pupil of the eye being examined.

9. The system for imaging the region of interest of the retina of the subject of claim 8 wherein the system for OCT and RBS fixation detection are configured such that OCT image collection is only executed during a period of foveal fixation of the subject.

10. The system for imaging the region of interest of the retina of the subject of claim 8 wherein the system for OCT and system for RBS fixation detection are configured such that data are continuously and synchronously recorded from the OCT system and from the RBS fixation detection system, whereby periods of foveal fixation detected by the RBS fixation detection system can be used to identify synchronized portions of the OCT data that will yield images of the region of interest of the retina.

11. The system for imaging the region of interest of the retina of the subject of claim 8 further comprising an image display device to attract and maintain interest of the subject toward a center of the RBS fixation detection system, such that the retinal region of interest, in known spatial relationship to the fovea, is imaged.

12. The system for imaging the region of interest of the retina of the subject of claim 8 wherein the system configured for RBS signals a presence of foveal fixation to the system configured for OCT, thus triggering data collection.

13. The system for imaging the region of interest of the retina of the subject of claim 8 further comprising the system configured for OCT and the system configured for RBS fixation detection being configured to cooperate in a specified alignment, such that when the RBS fixation detection system detects alignment with a fovea of the eye, the OCT system will be aimed at the retinal region of interest including a macular area.

14. A method for imaging a region of interest of a retina of a subject comprising:
 synchronizing an optical coherence tomography (OCT) system with a retinal birefringence scanning fixation detection (RBS) system;
 detecting foveal fixation with the RBS system;
 signaling detection of foveal fixation to the OCT system; and
 enabling OCT data collection during foveal fixation.

15. The method of claim 14 further comprising communicating between the two systems where OCT data is being collected continuously.

16. The method of claim 14 further comprising recording an additional synchro-channel from the RBS system.

17. The method of claim 14 further comprising carrying information about presence or absence of foveal fixation.

18. The method of claim 14 further comprising processing only time intervals of foveal fixation, during RB S-guided OCT analysis and reconstruction, thus reducing analysis time.

19. The method of claim 14 further comprising presenting fixation targets to the test subject during OCT data collection with a continuous movie aligned with a center of said RBS fixation detection scan, such that specific attention/fixation-locking targets appear periodically in the center of a display screen while the continuous movie fades away.

20. The method of claim 14 further comprising optimizing the method for use with children and subjects that cannot remain still.

* * * * *